United States Patent
Amino et al.

(10) Patent No.: US 7,238,830 B2
(45) Date of Patent: * Jul. 3, 2007

(54) N-ALKYLASPARTYL DIPEPTIDE ESTER COMPOUNDS

(75) Inventors: Yusuke Amino, Kawasaki (JP); Kazuko Yuzawa, Kawasaki (JP); Tadashi Takemoto, Kawasaki (JP); Ryoichiro Nakamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 834 days.

This patent is subject to a terminal disclaimer.

(21) Appl. No.: 09/809,197

(22) Filed: Mar. 16, 2001

(65) Prior Publication Data

US 2001/0039357 A1 Nov. 8, 2001

Related U.S. Application Data

(63) Continuation of application No. PCT/JP99/04977, filed on Sep. 10, 1999.

(30) Foreign Application Priority Data

Sep. 18, 1998 (JP) ............................................ 10-264252
Jun. 16, 1999 (JP) ............................................ 11-169419

(51) Int. Cl.
*C07C 229/00* (2006.01)
*A23L 1/236* (2006.01)

(52) U.S. Cl. .............................. 560/38; 560/41; 560/44; 562/443; 426/548

(58) Field of Classification Search .................. 560/38, 560/41, 44; 420/548; 544/322; 558/412; 562/443; 426/548; 549/441
See application file for complete search history.

(56) References Cited

U.S. PATENT DOCUMENTS

| 4,645,678 | A | 2/1987 | Nofre et al. |
| 4,766,246 | A | 8/1988 | Zanno et al. |
| 5,480,668 | A | 1/1996 | Nofre et al. |
| 5,968,581 | A | 10/1999 | Nakamura et al. |
| 6,649,784 | B2 | 11/2003 | Amino et al. |

FOREIGN PATENT DOCUMENTS

| EP | 0 691 346 | 1/1996 |
| EP | 0 784 050 | 7/1997 |
| EP | 0 818 463 | 1/1998 |
| GB | 1 206 233 | 9/1970 |
| HU | 204 418 B | 4/1989 |
| HU | 218 158 B | 3/1996 |
| JP | 8-503206 | 4/1996 |

OTHER PUBLICATIONS

U.S. Ser. No. 10/117,196, filed on Apr. 8, 2002, inventor Nagashima et al.
U.S. Ser. No. 09/809,197, filed Mar. 16, 2001, inventor Amino et al.
U.S. Ser. No. 10/656,228, filed Sep. 8, 2003, inventor Amino et al.
U.S. Ser. No. 10/177,205, filed Apr. 8, 2002, inventor Kawahara et al.

*Primary Examiner*—Taylor Victor Oh
(74) *Attorney, Agent, or Firm*—Oblon, Spivak, McClelland, Maier & Neustadt, P.C.

(57) ABSTRACT

The present invention provides N-alkylaspartyl dipeptideester compounds and salts thereof, such as N-[N-[3-(3-hydroxy-4-methoxyphenyl)-3-methylbutyl]-L-α-aspartyl]-L-phenylalanine 1-methyl ester, which provide high degrees of sweetness in comparison to conventional products, compositions and products containing the novel aspartyl dipeptide ester compounds and method of producing the novel aspartyl dipeptide ester compounds.

62 Claims, No Drawings

N-ALKYLASPARTYL DIPEPTIDE ESTER COMPOUNDS

This application is a Continuation International Application No. PCT/JP99/04977 Filed on Sep. 10, 1999.

BACKGROUND OF THE INVENTION

1. Field of the Invention

This invention relates to a novel N-alkylaspartyl dipeptide ester compounds, a sweetening agent or a sweetened food or similar products comprising the compound as an effective component. The invention further provides methods of imparting sweetness in a product and methods of making the N-alkylaspartyl dipeptide ester compounds.

2. Discussion of the Background

In recent years, as eating habits and products eaten have changed, fatness caused by excessive sugar intake and diseases caused by fatness have been of significant concern. Accordingly, the development of a low-calory sweetener (sweetening agent) that replaces sugar has been in demand. A sweetener that has been widely used is aspartame which is excellent in safety, quality of sweetness and taste properties. However, there are problems with aspartame with respect to its stability. WO 94/11391 states that compounds in which an alkyl group is introduced on a nitrogen atom of aspartic acid in the aspartame markedly improves the sweetening potency and also results in a slight improvement in the stability of the compound. The best compound described in WO 94/11391 is N-[N-(3,3-dimethylbutyl)-L-α-aspartyl]-L-phenylalanine 1-methyl ester having a 3,3-dimethylbutyl group as an alkyl group and which has a sweetening potency of 10,000 times that of sucrose (the value is obtained by comparing the compound to 2%, 5% and 10% sucrose solutions).

Aspartame compounds having 20 different substituents other than the 3,3-dimethylbutyl group are also disclosed where the compounds have sweetening potencies less than 2,500 times that of sucrose. Compounds having a 3-(substituted phenyl) propyl group as an alkyl group are also shown. Among these, N-[N-(3-phenylpropyl)-L-(α-aspartyl]-L-phenylalanine 1-methyl ester and N-[N-(3-(3-methoxy-4-hydroxyphenylpropyl)-L-α-aspartyl]-L-phenylalanine 1-methyl ester are described as having sweetening potencies of 1500 and 2500 times that of sucrose, respectively. These sweetening potencies are far less than that of N-[N-(3,3-dimethylbutyl)-L-α-aspartyl]-L-phenylalanine 1-methyl ester, which is 10,000 times that of sucrose. Further described are N-[N-[(RS)-3-phenylbutyl]-L-(α-aspartyl]-L-phenylalanine 1-methylester, which has as an alkyl group a 3-phenyl propyl group to the third position of which a methyl group is introduced, that is a 3-phenyl butyl group, is reported to have a sweetening potency of 1,200 times that of sucrose. The N-[N-(3-phenylpropyl)-L-α-aspartyl]-L-phenylalanine 1-methyl ester has a lower sweetening potency due to the methyl group introduced at the third position.

Furthermore, N-[N-[3-(3-methoxy-4-hydroxyphenyl)(RS)-1-methylpropyl]-L-α-aspartyl]-L-phenylalanine 1-methylester, having a structure corresponding to N-[N[3-(3-methoxy-4-hydroxyphenyl) propyl)-L-(α-aspartyl]-L-phenylalanine 1-methyl ester, with a methyl group on the first position of the propyl group is reported to have a sweetening potency of 500 times that of sucrose. The significantly lower sweetening potency is due to the methyl group on the the propyl group.

Another example of replacing the L-phenylalanine methyl ester moiety with another amino acid ester is N-[N-(3,3-dimethylbutyl)-L-α-aspartyl]-L-tyrosine 1-methyl ester which has a sweetening potency of 4,000 times that of sucrose.

In view of the foregoing, development of a low-calory sweetener having a superior sweetening potency is in demand.

Thus, the present inventors sought to solve the long-standing problems associated with prior low-calory sweeteners and provide novel N-alkylaspartyl dipeptide ester compounds which are excellent in safety and which have sweetening potencies equal to or higher than that of N-[N-(3,3-dimethylbutyl)-L-α-aspartyl]-L phenylalanine 1-methylester, and a low-calory sweetening agent comprising the compound as an effective component.

SUMMARY OF THE INVENTION

Accordingly, one object of the present invention is an N-alkylaspartyl dipeptide ester compound, and salts thereof, represented by formula (1):

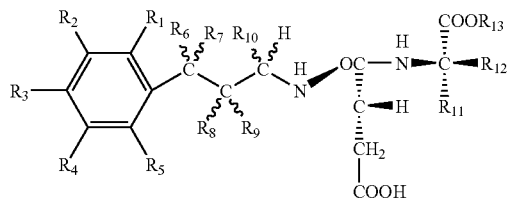

wherein $R_1$, $R_2$, $R_3$, $R_4$ and $R_5$ are independent from each other, selected from the group consisting of a hydrogen atom, a hydroxyl group, an alkoxy group having 1 to 3 carbon atoms, an alkyl group having 1 to 3 carbon atoms and a hydroxy alkyloxy group having two or three carbon atoms, and $R_1$ and $R_2$, or $R_2$ and $R_3$, optionally, form a methylene dioxy group, and $R_4$ and $R_5$, and $R_1$ or $R_3$ which do not form the methylene dioxy group are defined as above;

$R_6$, $R_7$, $R_8$, $R_9$ and $R_{10}$ are independent from each other, a hydrogen atom or an alkyl group with 1 to 3 carbon atoms; and optionally, two of $R_6$, $R_7$, $R_8$, $R_9$ and $R_{10}$ may combine to form an alkylene group with 1 to 5 carbon atoms, and $R_6$, $R_7$, $R_8$, $R_9$ and $R_{10}$ which do not form the alkylene group with 1 to 5 carbon atoms are defined as above;

$R_{11}$ is selected from the group consisting of a hydrogen atom, a benzyl group, a p-hydroxy benzyl group, a cyclohexyl methyl group, a phenyl group, a cyclohexyl group, a phenyl ethyl group and a cyclohexyl ethyl group;

$R_{12}$ is selected from the group consisting of a hydrogen atom and an alkyl group with 1 to 3 carbon atoms; and $R_{13}$ is selected from the group consisting of alkyl groups with 1 to 4 carbon atoms;

with the proviso that the following are excluded:

where $R_6$, $R_7$, $R_8$, $R_9$ and $R_{10}$ are a hydrogen atom at the same time, where $R_6$ is a methyl group, $R_1$, $R_2$, $R_3$, $R_4$, $R_5$, $R_7$, $R_8$, $R_9$, $R_{10}$ and $R_{12}$ are a hydrogen atom at the same time and $R_{11}$ is a benzyl group or a p-hydroxy benzyl group, at the same time; and where $R_2$ or $R_4$ is a methoxy group, $R_3$ is a hydroxyl group, $R_{10}$ is a methyl group, $R_1$, $R_4$ or $R_2$, $R_5$, $R_6$, $R_7$, $R_8$ and $R_9$ are hydrogen atoms at the same time, and $R_{11}$ is a benzyl group or a p-hydroxy benzyl group.

Other objects of the present inventions include compositions comprising the N-alkylaspartyl dipeptide ester compound, methods of imparting sweetness into a substance by adding the N-alkylaspartyl dipeptide ester compound to the substance and methods of making the N-alkylaspartyl dipeptide ester compound.

DETAILED DESCRIPTION OF THE INVENTION

Each document, patent application or patent publication cited by or referred to in this disclosure is incorporated by reference in its entirety.

For resolving the above problem, the present inventors have synthesized a variety of compounds in which a variety of 3-(substituted phenyl) propyl group, such as 3,3-dialkyl-3-(substituted phenyl) propyl groups or (RS)-3-alkyl-3-(substituted phenyl) propyl groups, have been introduced on a nitrogen atom of an aspartic acid constituting an aspartame and an aspartame compound, by reductive alkylation, using a 3-phenylpropionaldehyde compound, a cinnamaldehyde compound, a (2-phenylethyl) alkyl ketone compound or the like having a variety of substituents on a phenyl group and also having 1 to 4 alkyl substituents on the main chain, and examined the sweetening potency of these compounds. The compound corresponds to the aspartame the L-phenylalanine methyl ester moiety of which is substituted by another amino acid ester therein. As a result of our investigations, the sweetening potency of some of the aspartame compounds is much higher in sweetening potency than N-[N-(3,3-dimethylbutyl)-L-α-aspartyl]-L-phenylalanine 1-methylester reported to have the sweetening potency of 10000 times that of sucrose, to say nothing of N-[N-[(RS)-3-phenylbutyl]-L-(α-aspartyl]-L-phenylalanine 1-methylester reported to have the sweetening potency of 1200 times that of sucrose or N-[N-(3,3-dimethylbutyl)-L-α-aspartyl]-L-tyrosine 1-methylester reported to have a sweetening potency equal to 4000 times that of sucrose, as disclosed in the international Patent Publication WO 94/11391, and that, in particular, the compound represented by the general formula (1) below is superior as a sweetening agent.

The novel N-alkylaspartyl dipeptide ester compound according to the present invention includes compounds represented by the above formula (1) and salts thereof. Preferably, the amino acids in the compound of formula (1), aspartic acid, is in the L-isomer. Other amino acids may be in the L- or D-isomer, as desired.

In the compounds of the present invention substituents are defined as known in the art and include a hydrogen atom (H), a hydroxyl group (OH), an alkoxy group with 1 to 3 carbon atoms ($OCH_3$, $OCH_2CH_3$, $OCH_2CH_2CH_3$, etc.), an alkyl group with 1 to 3 carbon atoms ($CH_3$, $CH_2CH_3$, $CH_2CH_2CH_3$, etc.), a hydroxy alkyloxy group with two or three carbon atoms ($O(CH_2)2OH$, $OCH_2CH(OH)CH_3$, etc.), a methylene dioxy group ($OCH_2O$) and an alkylene group with 1 to 5 carbon atoms (such as $CH_2$, $CH_2CH_2$, $CH_2CH_2CH_2$ and so forth).

Preferred substituents in the compounds of formula (1) include:

(1) $R_6$ is a methyl group.
(2) $R_7$ is a methyl group.
(3) $R_8$, $R_9$ and $R_{10}$ are hydrogen atoms.
(4) $R_{10}$ is a methyl group.
(5) $R_6$ and $R_7$ combine to form an alkylene group having 1 to 5 carbon atoms.
(6) Above compounds (1), not containing the compounds wherein $R_1$, $R_2$, $R_3$, $R_4$ and $R_5$ are hydrogen atoms.
(7) $R_6$ is a methyl group and $R_1$, $R_2$, $R_3$, $R_4$, $R_5$, $R_7$, $R_8$, $R_9$ and $R_{10}$ are hydrogen atoms.
(8) $R_6$ is an alkyl group having two or three carbon atoms.
(9) Two of $R_6$, $R_7$, $R_8$, $R_9$ and $R_{10}$ combined to form an alkylene group with one to five carbon atoms.
(10) $R_6$, $R_7$, $R_8$, $R_9$ are hydrogen atoms, $R_{10}$ is a methyl group, $R_2$ is a hydrogen atom; a hydroxyl group; an alkoxy group with two or three carbon atoms, an alkyl group with one to three carbon atoms, a hydroxy alkyloxy group having two or three carbon atoms; or $R_2$ combined with $R_1$ or $R_3$ is a methylene dioxy group.
(11) $R_6$, $R_7$, $R_8$ and $R_9$ are hydrogen atoms, $R_{10}$ is a methyl group, $R_3$ is a hydrogen atom, an alkoxy group with one to three carbon atom, an alkyl group with one to three carbon atoms and a hydroxy alkyloxy group having two or three carbon atoms; and $R_2$ may combine with $R_1$ or $R_3$ form a methylene dioxy group.
(12) $R_1$, $R_4$, $R_5$, $R_6$, $R_7$, $R_8$ and $R_9$ are hydrogen atoms, $R_{10}$ is a methyl group, $R_2$ is a methoxy group, $R_3$ is a hydroxyl group, and $R_{11}$ is a hydrogen atom, a cyclohexyl methyl group, a phenyl group, a cyclohexyl group, a phenylethyl ($CH_2CH_2C_6H_5$) and a cyclohexylethyl group ($CH_2CH_2C_6H_{11}$).
(13) $R_6$ and $R_7$, are hydrogen atoms and $R_{10}$ is an alkyl group with two or three carbon atoms.
(14) $R_6$ and $R_7$ are hydrogen atoms and two of $R_8$, $R_9$ and $R_{10}$ may combine to form an alkylene group with 1 to 5 carbon atoms.
(15) $R_6$, $R_7$ and $R_{10}$ are hydrogen atoms, at least one of $R_8$ and $R_9$ is an alkyl group with one to three carbon atoms or $R_8$ and $R_9$ combine to form an alkylene group with 1 to 5 carbon atoms.
(16) $R_3$ is a methoxy group, $R_1$, $R_2$, $R_4$, $R_5$, $R_7$, $R_8$, $R_9$, $R_{10}$ and $R_{12}$ are hydrogen atoms, $R_6$ and $R_{13}$ are a methyl groups and $R_{11}$ is a benzyl group.
(17) $R_2$ is a hydroxyl group, $R_1$, $R_3$, $R_4$, $R_5$, $R_7$, $R_8$, $R_9$, $R_{10}$ and $R_{12}$ are hydrogen atoms, $R_6$ and $R_{13}$ is a methyl group, and $R_{11}$ is a benzyl group.
(18) $R_2$ is a methoxy group, $R_3$ is a hydroxyl group, $R_1$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a benzyl group.
(19) $R_2$ is a hydroxyl group, $R_3$ is a methoxy group, $R_1$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a benzyl group.
(20) $R_2$ is a methoxy group, $R_3$ is a hydroxyl group, $R_1$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a p-hydroxybenzyl group.
(21) $R_2$ is a hydroxyl group, $R_3$ is a methoxy group, $R_1$, $R_4$, $R_5$, $R_7$, $R_8$, $R_9$, $R_{10}$ and $R_{12}$ is a hydrogen atom, $R_6$ and $R_{13}$ are methyl groups and $R_{11}$ is a cyclohexylmethyl group.
(22) $R_3$ is a methoxy group, $R_1$, $R_2$, $R_4$, $R_5$, $R_8$, $R_9$, $R_{10}$ and $R_{12}$ are hydrogen atoms, $R_6$, $R_7$ and $R_{13}$ are a methyl groups, and $R_{11}$ is a benzyl group.
(23) $R_3$ is a hydroxyl group, $R_1$, $R_2$, $R_4$, $R_5$, $R_8$, $R_9$, $R_{10}$ and $R_{12}$ are hydrogen atoms, $R_6$, $R_7$ and $R_{13}$ are methyl groups and $R_{11}$ is a benzyl group.
(24) $R_2$ is a methoxy group, $R_3$ is a hydroxyl group, $R_1$, $R_4$, $R_5$, $R_8$, $R_9$, $R_{10}$ and $R_{12}$ are hydrogen groups, $R_6$, $R_7$ and $R_{13}$ are methyl group sand $R_{11}$ is a benzyl group.
(25) $R_2$ is a hydroxyl group, $R_3$ is a methoxy group, $R_1$, $R_4$, $R_5$, $R_8$, $R_9$, $R_{10}$ and $R_{12}$ are hydrogen groups, $R_6$, $R_7$ and $R_{13}$ are methyl groups and $R_{11}$ is a benzyl group.
(26) $R_2$ is a methyl group, $R_3$ is a hydroxyl group, $R_1$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a benzyl group.
(27) $R_2$ is a hydroxyl group, $R_3$ is a methoxy group, $R_1$, $R_4$, $R_5$, $R_6$, $R_7$, $R_9$, $R_{10}$ and $R_{12}$ are hydrogen atoms, $R_8$ and $R_{13}$ are methyl groups and $R_{11}$ is a benzyl group.

(28) $R_1$ is a hydroxyl group, $R_2$, $R_3$, $R_4$, $R_5$, $R_8$, $R_9$, $R_{10}$ and $R_{12}$ are hydrogen atoms, $R_6$, $R_7$ and $R_{13}$ are methyl groups and $R_{11}$ is a benzyl group.

(29) $R_1$ is a hydroxyl group, $R_3$ is a methoxy group, $R_2$, $R_4$, $R_5$, $R_8$, $R_9$, $R_{10}$ and $R_{12}$ are hydrogen atoms, $R_6$, $R_7$ and $R_{13}$ are methyl groups and $R_{11}$ is a benzyl group.

(30) $R_1$ is a hydroxyl group, $R_3$ is a methyl group, $R_2$, $R_4$, $R_5$, $R_6$, $R_9$, $R_{10}$ $R_{10}$ and $R_{12}$ are hydrogen atoms, $R_6$, $R_7$ and $R_{13}$ are methyl groups and $R_{11}$ is a benzyl group.

(31) $R_2$ and $R_3$ combine to form a methylene dioxy group, $R_1$, $R_4$, $R_5$, $R_8$, $R_9$, $R_{10}$ and $R_{12}$ are hydrogen atoms, $R_6$, $R_7$ and $R_{13}$ are methyl groups and $R_{11}$ is a benzyl group.

(32) $R_2$ is a methyl group, $R_3$ is a methoxy group, $R_1$, $R_4$, $R_5$, $R_8$, $R_9$, $R_{10}$ and $R_{12}$ are hydrogen atoms, $R_6$, $R_7$ and $R_{13}$ are methyl groups and $R_{11}$ is a benzyl group.

(33) $R_2$ is a methyl group, $R_3$ is a hydroxyl group, $R_1$, $R_4$, $R_5$, $R_8$, $R_9$, $R_{10}$ and $R_{12}$ are are hydrogen atoms, $R_6$, $R_7$ and $R_{13}$ are methyl groups, and $R_{11}$ is a benzyl group.

(34) $R_2$ is a hydroxyl group, $R_3$ is a methyl group, $R_1$, $R_4$, $R_5$, $R_8$, $R_9$, $R_{10}$ and $R_{12}$ are hydrogen atoms, $R_6$, $R_7$ and $R_{13}$ are methyl groups and $R_{11}$ is a benzyl group.

(35) $R_2$ is a methoxy group, $R_3$ is a hydroxyl group, $R_1$, $R_4$, $R_5$, $R_8$, $R_9$, $R_{10}$ and $R_{12}$ are hydrogen groups, $R_6$ and $R_7$ combine to form a tetramethylene group, $R_{11}$ is a benzyl group and $R_{13}$ is a methyl group.

(36) $R_2$ is a hydroxyl group, $R_3$ is a methoxy group, $R_1$, $R_4$, $R_5$, $R_8$, $R_9$, $R_{10}$ and $R_{12}$ are hydrogen atoms, $R_6$ and $R_7$ are methyl groups, $R_{11}$ is a benzyl group and $R_{13}$ is an ethyl group.

(37) $R_2$ and $R_3$ are hydroxyl groups, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

(38) $R_2$ is a hydroxyl group, $R_3$ is a methoxy group, $R_1$, $R_4$, $R_5$, $R_8$, $R_9$ and $R_{10}$ are hydrogen atoms, $R_6$, $R_7$, $R_{12}$ and $R_{13}$ are methyl groups and $R_{11}$ is a benzyl group.

(39) In the compounds of formula (1), particularly with substituents listed in (16) through (21) and (26) the carbon atom to which $R_8$ is linked is in the (R), (S), (RS) configuration or the like.

(40) In the compounds of formula (1), particularly with substituents listed in (27) the carbon atom to which is $R_8$ linked in the formula is in the (R), (S), (RS) configuration or the like.

(41) The carbon atom to which $R_{10}$ is linked in the formula (1) is in the (R), (S), (RS) configuration or the like.

Compositions according to the present invention contain one or more of the compounds of formula (1). When the compounds (including compounds in the present invention and the salts thereof) of the present invention are used as sweeteners, these may of course be used in combination with other sweeteners as desired or needed.

Additional embodiments of the present invention include compositions containing the compound of formula (1) where such compositions contain additives, stabilizers, carriers and the like which are commonly used in the art.

When the compounds of the present invention are used as sweeteners, an appropriate carrier and/or an appropriate bulking agent may be used as required. For example, a carrier, a bulking agent or the like which is known in the art and so far used for the sweeteners is available. The appropriate carriers or bulking agent may be selected from polydextrose, starch, maltodextrines, cellulose, methylcellulose, carboxymethylcellulose and other cellulose compounds, sodium alginate, pectins, gums, lactose, maltose, glucose, sucrose, leucine, glycerole, mannitol, sorbitol, xylitol, erythritol, and equivalents thereof.

The compounds of the present invention can be used as sweeteners or ingredients therefor, and further as sweeteners for products such as foods, beverages and the like to which a sweetness has to be imparted. Examples of such products include soft-drinks, fruit juices, teas, water, confectioneries, chewing gum, hygiene products, toiletries, cosmetics, pharmaceutical products and veterinary products for animals. Still further, they can be used as a form of products having sweetness including the compounds of the present invention and they can be used in a method of imparting sweetness to the products requiring sweetness. The method therefor can be, known methods for example, conventional methods for using a sweetening ingredient for a sweetener in the sweeteners or the method of imparting sweetness. Accordingly, a preferred embodiment of the present invention is a method of imparting sweetness in a substance or a product by adding one or more of the compounds of formula (1) to said substance or product. Such substances or products include those described above.

The compound of formula (1), where $R_{10}$ is a hydrogen atom, can be prepared by reacting under reductive alkylation conditions an aldehyde having the formula (2):

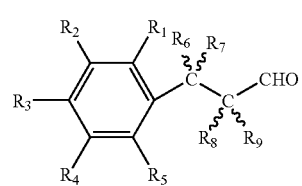

(2)

where $R_1$, $R_2$, $R_3$, $R_4$, $R_5$, $R_6$, $R_7$, $R_8$ and $R_9$ have the same meaning as $R_1$, $R_2$, $R_3$, $R_4$, $R_5$, $R_6$, $R_7$, $R_8$ and $R_9$, respectively in the above formula (1); and if $R_6$ and $R_7$, or $R_8$ and $R_9$ are not the same substituents, there is no particular limitation to the configuration of carbon atoms to which $R_6$ and $R_7$, or $R_8$ and $R_9$ are linked, such that it may be (R), (S), (RS) or the like whichever is desired;

with an aspartame compound shown by the following general formula (3):

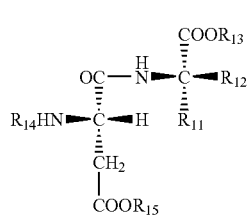

(3)

wherein $R_{11}$, $R_{12}$ and $R_{13}$ in the above formula (3) have the same meaning as $R_{11}$, $R_{12}$ and $R_{13}$, respectively in the above formula (1), $R_14$ denotes a hydrogen atom or a substituent that can be converted into a hydrogen atom under the reductive alkylation condition and $R_{15}$ denotes a hydrogen atom, a benzyl group or a substituent that may be used for protecting a carboxyl group such as a t-butyl group or the like.

The compound of formula (1), where $R_7$, $R_9$ and $R_{10}$ are hydrogen atoms can be prepared by reacting under reductive alkylating conditions, an aldehyde having the formula (4)

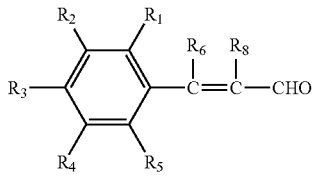

(4)

where $R_1$, $R_2$, $R_3$, $R_4$, $R_5$, $R_6$ and $R_8$ have the same meaning as $R_1$, $R_2$, $R_3$, $R_4$, $R_5$, $R_6$ and $R_8$, respectively in the above formula (1);

with an aspartame compound shown by the above-mentioned general formula (3).

The compound of formula (1) where $R_{10}$ is a hydrogen atom, can be prepared by reacting under reductive alkylating conditions, an aldehyde having formula (5):

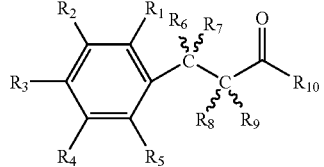

(5)

where $R_1$, $R_2$, $R_3$, $R_4$, $R_5$, $R_6$, $R_7$, $R_8$, $R_9$ and $R_{10}$ have the same meanings as $R_1$, $R_2$, $R_3$, $R_4$, $R_5$, $R_6$, $R_7$, $R_8$, $R_9$ and $R_{10}$, respectively in formula (1);

it being noted that, if $R_6$ and, $R_7$, or $R_8$ and $R_9$ are not the same substituents, there is no particular limitation to the configuration of the carbon atoms to which $R_6$ and $R_7$, or $R_8$ and $R_9$ are linked, such that it may be (R), (S), (RS) or the like whichever is desired;

with the aspartame compound shown by the above general formula (3).

The aforementioned methods of preparing the compounds of formula (1) include a reacting step under the reductive alkylation conditions, and may also include other reactive steps. An additional step or steps may be included, following the reacting step under the reductive alkylation condition, for example, de-protection in a hydroxyl group or the other functional group and/or a salt forming step or the like. Such methods of protection and deprotection can be performed as described in T. W. Greene and P. G. M. Wuts, "Protective Groups in Organic Synthesis", John Wiley and Sons, Inc. (1999).

As the substituent that can be converted into a hydrogen atom under the reductive alkylation condition, those that are known in the art which can be used for such purpose, e.g., benzyloxy carbonyl group or the like, may be optionally selected depending on the particular reductive alkylation conditions employed in the reaction. As these reductive alkylation conditions, the conditions as known in the art, or any suitable conditions that will be developed in future, such as a condition employing metal hydrides, may be used, as needed.

Additional embodiments of the present invention, if aldehydes shown by the general formulas (2), (4) or (5) include hydroxyl groups, the aforementioned preparation methods may employ an aldehyde, the hydroxyl group of which is protected by a suitable protecting group, such as benzyl group.

Salts of the compounds of the present invention include, for example, salts of alkali metals such as sodium and potassium, salts of alkali earth metals, such as calcium and magnesium, ammonium salt with ammonia, salts with amino acids, such as lysine and arginine, salts with inorganic acids, such as hydrogen chloride and sulfuric acid, salts with organic acids, such as citric acid and acetic acid, and salts with sweetening agents, such as saccharin, acesulfame, cyclamic acid and glycyrrhizic acid. The preparation of the salts of the present compound of formula(1) can be prepared as known in the art.

The N-alkylaspartyl dipeptide ester compound of the present invention can be synthesized by reductive alkylation of aspartame or aspartame compounds, that is compounds obtained by replacing an L-phenylalanine methylester moiety in the aspartame by another amino acid ester, using a 3-phenylpropionaldehyde compound, a cinnamaldehyde compound or a (2-phenylethyl) alkylketone compound, which has different substituents on a phenyl group and also having one to four alkyl substituents on the main chain, and a reducing agent, such as a hydrogen/palladium carbon catalyst. Alternatively, the N-alkylaspartyl dipeptide ester compound of the present invention can be produced by reductive alkylation of an aspartame compound, having a protecting group in a β-position in the carboxylic acid, such as β-O-benzyl-α-L-aspartyl-L-amino acid methyl ester, using the above-described 3-phenylpropionaldehyde compound, a cinnamaldehyde compound or a (2-phenylethyl) alkylketone compound, and a reducing agent, such as $NaB(OAc)_3H$, as disclosed in A. F. Abdel-Magid et al., Tetrahedron letters, 31, 5595 (1990), followed by removal of protecting groups thereof, or by a method consisting in saturating unsaturated bonds with a reducing agent, as the occasion may demand. The above aspartame compound may be obtained by a usual peptide synthesis method, as discussed in Izumiya et al., Fundamentals and Experimentation in Peptide Synthesis. Published by MARUZEN on Jan. 20, 1985. The method for synthesis of the compounds in the present invention is, however, not limited to these methods. In place of the above-mentioned 3-phenylpropionaldehyde compound, cinnamaldehyde compound or the (2-phenylethyl) alkyl ketone compound, acetal or ketal compounds thereof may, of course, be used as the aldehyde or ketone components at the time of the reductive alkylation.

As a result of sensory evaluation, the present compounds and salts thereof were found to have strong sweetening potency and have sensory (organoleptic) properties similar to that of sugar. For example, the sweetness of N-[N-[3-(3-hydroxy-4-methoxyphenyl)-3-methylbutyl]-L-α-aspartyl]-L-phenylalanine 1-methyl ester was approximately 70000 times that of sugar, the sweetness of N-[N-[3-(3-methyl-4 hydroxyphenyl)-3-methylbutyl]-L-α-aspartyl]-L-phenylalanine 1-methyl ester was approximately 70000 times that of sugar, the sweetness of N-[N-[3-(3-hydroxy-4-methylphenyl)-3-methylbutyl]-L-α- aspartyl]-L-phenylalanine 1-methyl ester was approximately 60000 times that of sugar, and the sweetness of N-[N-((RS)-3-(3 hydroxy-4-methoxyphenyl) butyl]-L-α-aspartyl]-L-phenylalanine 1-methyl ester was approximately 50000 times that of sugar. On the other hand, the half life in a buffer of pH=3.0 at 72.0° C. of N-[N-[3-(3-methoxy-4-hydroxyphenyl)-3-methylbutyl]-L-α-aspartyl]-L-phenylalanine 1-methyl ester was 34.4 hours, which was substantially equivalent to the half life of N-[N-(3,3-dimethylbutyl)-L-α-aspartyl]-L-phenylalanine 1-methyl ester (31.4 hours under the same condition). Also, the half life in a buffer with pH=3.0 at 70.0° C. of aspartame, N-[N-(3,3-dimethylbutyl)-L-α-aspartyl]-L-phenylalanine 1-methyl ester, N-[N-[3-(3-hydroxy-4-methoxyphenyl)-3-methylbutyl]-L-α-aspartyl]-L-phenylalanine 1- methyl ester and N-[N-(3-(4-hydroxyphenyl)-3-methylbutyl]-L-α-aspartyl)-L-phenylalanine 1-methylester, was measured, and found to be 23.5, 38.3, 44.5 and 43.6 hours, respectively. Sensory evaluations can be performed as described in, for example, B. T. Carr, S. D. Pecore, K. M. Gibes and G. E. Dubois, "Sensory Methods for Sweetner Evaluation" in *Flavor Measurement*, edited by C. T. Ho and C. H. Manley, Marcel Decker, Inc. (1992).

The present application is a Continuation Application of PCT/JP99/04977 filed Sep. 10, 1999 which claims priority to JP10-264252 filed Sep. 18, 1998 and JP11-169419 filed Jun. 16, 1999. The contents of theses documents are herein incorporated by reference into the present specification Having generally described this invention, a further understanding can be obtained by reference to certain specific examples which are provided herein for purposes of illustration only, and are not intended to be limiting unless otherwise specified.

EXAMPLES

In the following examples, the NMR spectra were measured using Varian Gemini 300 (300 MHz) and MS spectra were measured using Thermo Quest TSQ700.

Example 1

Synthesis of N-[N-[3-(3-hydroxy-4-methoxyphenyl)-3-methylbutyl]-L-α-aspartyl]-L-phenylalanine 1-methyl ester (Table 1, compound number 10)

To 703 mg (1.45 mmol) of N-t-butoxycarbonyl-β-o-benzyl-(α-L-aspartyl-L-phenylalanine methyl ester, 10 ml of a 4 N-HCl/dioxane solution were added and stirred at room temperature for one hour. The reaction solution was concentrated under reduced pressure. To the residue were added 50 ml of a 5%-aqueous solution of sodium hydrogen carbonate and extraction was made twice with 50 ml of ethyl acetate. An organic layer was washed with a saturated saline water and dried over anhydrous magnesium sulfate. Magnesium sulfate was filtered off and the liquid filtrate was concentrated under reduced pressure to yield 557 mg (1.45 mmol) of (3-O-benzyl-(α-L-aspartyl-L-phenylalanine methyl ester, as a viscous oily substance.

557 mg (1.45 mmol) of the above β-O-benzyl-α-L-aspartyl-L-phenylalanine methyl ester were dissolved in 15 ml of tetrahydrofuran (THF) to yield a solution which was maintained at 0° C. To this solution were added 432 mg (1.45 mmol) of 3-(3-benzyloxy-4-methoxyphenyl)-3-methylbutyl aldehyde, 0.083 ml (1.45 mmol) of acetic acid and 462 mg (2.18 mmol) of NaB(OAc)$_3$H and stirred for one hour at 0 ° C. and overnight at room temperature. To the reaction solution were added 50 ml of a saturated aqueous solution of sodium hydrogen carbonate and extraction was made twice with 50 ml of ethyl acetate. An organic layer was washed with a saturated saline water and dried over anhydrous magnesium sulfate. Magnesium sulfate was filtered off and the liquid filtrate was concentrated under reduced pressure. The residue was purified with preparative thin layer chromatography (PTLC) to yield 832 mg (1.25 mmol) of N-[N-[3-(3-benzyloxy-4-methoxyphenyl)-3-methylbutyl]-(3-O-benzyl-L-α-aspartyl]-L-phenylalanine 1-methylester as a viscous oily substance.

The above 832 mg (1.25 mmol) of N-[N-[3-(3-benzyloxy-4-methoxyphenyl)-3-methylbutyl]-β-O-benzyl-L-α-aspartyl]-L-phenylalanine 1-methyl ester were dissolved in a mixed solvent of 25 ml of methanol and 2 ml of water, and 350 mg of 10% palladium carbon (containing 50% of water) were added thereto. The resulting mixture was reduced at room temperature for three hours under a hydrogen atmosphere. The catalyst was filtered off and the filtrate was concentrated under reduced pressure. The residue was purified with PTLC to remove an odor adsorbed to yield 400 mg (0.82 mmol) of N-[N-[3-(3-hydroxy-4-methoxyphenyl)-3-methylbutyl]-L-α-L-aspartyl)-L-phenylalanine L-methylester as a solid substance.

$^1$HMMR (DMSO-d$_6$) δ: 1.14 (s, 6H), 1.54–1.68 (m, 2H), 2.04–2.22 (m, 3H), 2.24–2.34 (dd, 1H), 2.84–2.94 (dd, 1H), 3.00–3.08 (dd, 1H), 3.31–3.36 (m, 1H), 3.59 (s, 3H), 3.71 (s, 3H), 4.46–4.55 (m, 1H), 6.60–6.65 (dd, 1H), 6.73 (s, 1H), 6.80 (d, 1H), 7.10–7.28 (m, 5H), 8.45 (d, 1H), 8.75 (brs, 1H). ESI (Electrospray Ionization)-MS 487.3 (MH$^+$)

Sweetness (sweetening potency), 70000 times the sweetness of sugar

Example 2

Synthesis of N-[N- [3-(4-methoxyphenyl)-3-methylbutyl]-L-α-aspartyl)-L-phenylalanine 1-methyl ester (Table 1, compound number 7)

N-[N-[3-(4-methoxyphenyl)-3-methylbutyl)-L-α-aspartyl]-L-phenylalanine 1-methyl ester was obtained as a solid substance, with a total yield of 72.2%, in the same way as in Example 1, except using 3-(4-methoxyphenyl)-3-methylbutyl aldehyde in place of 3-(3-benzyloxy-4-methoxyphenyl)-3-methylbutyl aldehyde.

$^1$HMMR (DMSO-d$_6$) δ: 1.17 (s, 6H), 1.62–1.72 (m, 2H), 2.04–2.20 (m, 3H), 2.24–2.34 (dd, 1H), 2.84–2.94 (dd, 1H), 2.95–3.07 (dd, 1H), 3.30–3.35 (m, 1H), 3.51 (s, 3H), 3.70 (s, 3H), 4.46–4.54 (m, 1H), 6.83 (d, 2H). 7.14–7.28 (m, 7H), 8.43 (d, 1H). ESI-MS 471.3 (MH$^+$)

Sweetness, 25000 times the sweetness of sugar

Example 3

Synthesis of N-[N-[3-(4-hydroxyphenyl)-3-methylbutyl]-L-α-aspartyl]-L-phenylalanine 1 methyl ester (Table 1, compound number 8)

N-[N-[3-(4-hydroxyphenyl)-3-methylbutyl]-L-α-aspartyl]-L-phenylalanine 1-methyl ester was obtained as a solid substance, with a total yield of 64.5%, in the same way as in Example 1, except using 3-(4-benzyloxyphenyl)-3-methylbutyl aldehyde in place of 3-(3-benzyloxy-4-methoxyphenyl)-3-methylbutyl aldehyde.

$^1$HMMR (DMSO-d$_6$) δ: 1.15 (s, 6H), 1.58–1.72 (m, 2H), 2.04–2.20 (m, 3H), 2.24–2.34 (dd, 1H), 2.85–2.94 (dd, 1H), 3.00–3.08 (dd, 1H), 3.30–3.36 (m, 1H), 3.59 (s, 3H), 4.46–4.55 (m, 1H), 6.67 (d, 2H), 7.07 (d, 2H), 7.10–7.27 (m, 5 H), 8.44 (d, 1H), 9.15 (brs, 1H). ESI-MS 457.3 (MH$^+$)

Sweetness, 25000 times the sweetness of sugar

Example 4

Synthesis of N-[N-[3-(3-methoxy-4-hydroxyphenyl)-3-methylbutyl]-L-α-aspartyl)-L-phenylalanine 1 methyl ester (Table 1, compound number 9)

N-[N-[3-(3-methoxy-4-hydroxyphenyl)-3-methylbutyl]-L(α-aspartyl]-L-phenylalanine 1-methyl ester was obtained as a solid substance, with a total yield of 62.2%, in the same way as in Example 1, except using 3-(3-methoxy-4-benzyloxyphenyl)-3-methylbutyl aldehyde in place of 3-(3-benzyloxy-4-methoxyphenyl)-3-methylbutyl aldehyde.

$^1$HMMR (DMSO-d$_6$) δ: 1.17 (s, 6H), 1.63–1.72 (m, 2H), 2.08–2.22 (m, 3H), 2.25–2.33 (dd, 1H), 2.86–2.94 (dd, 1H), 3.00–3.08 (dd, 1H), 3.33–3.38 (m, 1H), 3.59 (s, 3H), 3.75 (s, 3H), 3.47–3.55 (m, 1H), 6.67 (s, 2H), 6.81 (s, 1H), 7.14–7.27 (m, 5H), 8.46 (d, 1H), 8.70 (brs, 1H). ESI-MS 487.3 (MH$^+$)

Sweetness, 40000 times the sweetness of sugar

Example 5

Synthesis of N-[N-[3-(3-hydroxy-4-methoxyphenyl)-3-methylbutyl]-L-α-aspartyl]-L-((α-methyl) phenylalanine 1-methylester (Table 1, compound number 22)

N-(N-[3-(3-hydroxy-4-methoxyphenyl)-3-methylbutyl]-L-α-aspartyl]-L-(α-methyl) phenylalanine 1-methyl ester was obtained as a solid substance, with a total yield of 77.2%, in the same way as in Example 1, except using N-t-butoxycarbonyl-β-O-benzyl-(α-L-aspartyl-L-(α-methyl) phenylalanine methyl ester in place of N-t-butoxy carbonyl-β-O-benzyl-α-L-aspartyl-L-phenylalanine methyl ester.

$^1$HMMR (DMSO-d$_6$) δ: 1.18 (s, 6H), 1.22 (s, 3H), 1.66–1.76 (m, 2H), 2.18–238 (m, 4H), 3.00 (d, 1H), 3.19 (d, 1H), 3.36–3.42 (m, 1H), 3.49 (s, 3H), 3.72 (s, 3H), 6.67 (dd, 1H), 6.74 (d, 1H), 6.80 (d, 1H), 7.02–7.06 (m, 2H), 7.20–7.30 (m, 3H), 8.29 (brs, 1H), 8.75 (brs, 1H). ESI-MS 501.3 (MH$^+$)

Sweetness, 40000 times the sweetness of sugar

Example 6

Synthesis of N-[N-[3-(2-hydroxyphenyl)-3-methylbutyl]-L-α-aspartyl]-L-phenylalanine 1-methyl ester (Table 1, compound number 13)

N-[N-[3-(2-hydroxyphenyl)-3-methylbutyl]-L-α-aspartyl]-L-phenylalanine 1-methyl ester was obtained as a solid substance, with a total yield of 64.5%, in the same way as in Example 1, except using 3-(2-benzyloxyphenyl)-3-methylbutyl aldehyde in place of 3-(3-benzyloxy-4-methoxyphenyl)-3-methylbutyl aldehyde.

$^1$HMMR (DMSO-d$_6$) δ: 1.26 (s, 6H), 1.84–2.30 (m, 6H), 2.88 (dd, 1H), 3.02 (dd, 1H), 3.32–3.38 (m, 1H), 3.59 (s, 3H), 4.45–4.54 (m, 1H), 6.68–6.78 (m, 3H), 6.96–7.06 (m, 2H), 7.12–7.30 (m, 5H), 8.50 (d, 1H), 9.30 (brs, 1H). ESI-MS 457.4 (MH$^+$)

Sweetness, 8000 times the sweetness of sugar

Example 7

Synthesis of N-[N-[3-(2-hydroxy-4-methoxyphenyl)-3-methylbutyl]-L-α-aspartyl]-L-phenylalanine 1-methyl ester (Table 1, compound number 14)

N-[N-[3-(2-hydroxy-4-methoxyphenyl)-3-methylbutyl]-L-α-aspartyl]-L-phenylalanine 1-methyl ester was obtained as a solid substance, with a total yield of 44.1%, in the same way as in Example 1, except using 3-(2-benzyloxy-4-methoxyphenyl)-3-methylbutyl aldehyde in place of 3-(3-benzyloxy-4-methoxy phenyl)-3-methylbutyl aldehyde.

$^1$HMMR (DMSO-d$_6$) δ: 1.22 (s, 6H), 1.82–2.20 (m, 5H), 2.26 (dd, 1H), 2.88 (dd, 1H), 3.01 (dd, 1H), 3.34–3.40 (m, 1H), 3.59 (s, 3H), 3.64 (s, 3H), 4.46–4.53 (m, 1H), 6.28 (dd, 1H), 6.36 (d, 1H), 6.92 (d, 1H), 7.14–7.26 (m, 5H), 8.52 (d, 1H), 9.40 (brs, 1H). ESI-MS 487.3 (MH$^+$)

Sweetness, 20000 times the sweetness of sugar

Example 8

Synthesis of N-[N-[3-(2-hydroxy-4-methylphenyl)-3-methylbutyl]-L-α-aspartyl]-L-phenylalanine 1-methyl ester (Table 1, compound number 15)

N-(N-[3-(2-hydroxy-4-methylphenyl)-3-methylbutyl]-L-α-aspartyl]-L-phenylalanine 1-methyl ester was obtained as a solid substance, with a total yield of 45.1%, in the same way as in Example 1, except using 3-(2-benzyloxy-4-methylphenyl)-3-methylbutyl aldehyde in place of 3-(3-benzyloxy-4-methoxyphenyl)-3-methylbutyl aldehyde.

$^1$HMMR (DMSO-d$_6$) δ: 1.23 (s, 6H), 1.82–2.20 (m, 5H), 2.14 (s, 3H), 2.25 (dd, 1H), 2.88 (dd, 1H), 3.01 (dd, 1H), 3.33–3.39 (m, 1H), 3.58 (s, 3H), 4.46–4.54 (m, 1H), 6.51 (d, 1H), 6.87 (s, 1H), 6.90 (d, 1H), 7.10–7.23 (m, 5H), 8.51 (d, 1H), 9.20 (brs, 1H). ESI-MS 471.2 (MH$^+$)

Sweetness, 25000 times the sweetness of sugar

Example 9

Synthesis of N-[N-[3-(3,4-methylenedioxyphenyl)-3-methylbutyl]-L-α-aspartyl]-L-phenylalanine-1-methyl ester (Table 1, compound number 16)

N-[N-[3-(3,4-methylenedioxyphenyl)-3-methylbutyl]-L-α-aspartyl]-L-phenylalanine 1-methyl ester was obtained as a solid substance, with a total yield of 69.7%, in the same way as in Example 1, except using 3-(3,4-methylenedioxy phenyl)-3-methylbutyl aldehyde in place of 3-(3-benzyloxy-4-methoxyphenyl)-3-methylbutyl aldehyde.

$^1$HMMR (DMSO-d$_6$) δ: 1.16 (s, 6H), 1.60–1.70 (m, 2H), 2.05–2.20 (m, 3H), 2.27 (dd, 1H), 2.89 (dd, 1H), 3.03 (dd, 1H), 3.31–3.35 (m, 1H), 3.59 (s, 3H), 4.46–4.54 (m, 1H), 5.94 (s, 2H), 6.72 (dd, 1H), 6.79 (d, 1H), 6.88 (d, 1H), 7.15–7.28 (m, 5H), 8.44 (d, 1H). ESI-MS 485.4 (MH$^+$)

Sweetness, 30000 times the sweetness of sugar

Example 10

Synthesis of N-[N-[3-(3-methyl-4-methoxyphenyl)-3-methylbutyl]-L-α-aspartyl]-L-phenylalanine 1-methyl ester (Table 1, compound number 17)

N-[N-[3-(3-methyl-4-methoxyphenyl)-3-methylbutyl]-L-α-aspartyl]-L-phenylalanine 1-methyl ester was obtained as a solid substance, with a total yield of 66.0%, in the same way as in Example 1, except using 3-(3-methyl-4-methoxyphenyl)-3-methylbutyl aldehyde in place of 3-(3-benzyloxy-4-methoxy phenyl)-3-methylbutyl aldehyde.

$^1$HMMR (DMSO-d$_6$) δ: 1.16 (s, 6H), 1.63–1.72 (m, 2H), 2.13 (s, 3H), 2.08–2.20 (m, 3H), 2.25–2.32 (dd, 1H), 2.85–2.95 (dd, 1H), 3.00–3.06 (dd, 1H), 3.31–3.36 (m, 1H), 3.59 (s, 3H), 3.73 (s, 3H), 4.47–4.55 (m, 1H), 6.79–6.82 (m, 1H), 7.03–7.06 (m, 2H), 7.15–7.27 (m, 5H), 8.44–8.47 (d, 1H). ESI-MS 485.5 (MH$^+$)

Sweetness, 30000 times the sweetness of sugar

Example 11

Synthesis of N-[N-[3-(3-methyl-4-hydroxyphenyl)-3-methylbutyl)-L-α-aspartyl]-L-phenylalanine 1-methyl ester (Table 1, compound number 18)

N-[N-[3-(3-methyl-4-hydroxyphenyl)-3-methylbutyl]-L-α-aspartyl]-L-phenylalanine 1-methyl ester was obtained as a solid substance, with a total yield of 63.2%, in the same way as in Example 1, except using 3-(3-methyl-4-benzyloxyphenyl)-3-methylbutyl aldehyde in place of 3-(3-benzyloxy-4-methoxyphenyl)-3-methylbutyl aldehyde.

$^1$HMMR (DMSO-$d_6$) δ: 1.14 (s, 6H), 1.59–1.68 (m, 2H), 2.09 (s, 3H), 2.09–2.18 (m, 3H), 2.25 (dd, 1H), 2.90 (dd, 1H), 3.02 (dd, 1H), 3.30–3.36 (m, 1H), 3.59 (s, 3H), 4.46–4.54 (m, 1H), 6.68 (d, 1H), 6.88 (dd, 1H), 6.96 (s, 1H), 6.14–6.73 (m, 5H), 8.46 (d, 1H), 9.01 (brs, 1H). ESI-MS 471.4 (MH$^+$)

Sweetness, 70000 times the sweetness of sugar

Example 12

Synthesis of N-[N-[2-[1-(3-methoxy-4-hydroxyphenyl) cyclopentyl]ethyl]-L-α-aspartyl]-L-phenylalanine 1-methyl ester (Table 1, compound number 20)

N-[N-(2-[1-(3-methoxy-4-hydroxyphenyl) cyclopentyl] ethyl]-L-α-aspartyl]-L-phenylalanine 1-methyl ester was obtained as a solid substance, with a total yield of 68.4%, in the same way as in Example 1, except using 2-[1-(3-methoxy-4-hydroxyphenyl) cyclopentyl]acetaldehyde in place of 3(3-benzyloxy-4-methoxyphenyl)-3-methylbutyl aldehyde.

$^1$HMMR (DMSO-$d_6$) δ: 1.48–1.82 (m, 10H), 2.00–2.16 (m, 3H), 2.24 (dd, 1H), 2.90 (dd, 1H), 3.01 (dd, 1H), 3.30–3.40 (m, 1H), 3.59 (s, 3H), 3.74 (s, 3H), 4.45–4.53 (m, 1H), 6.59 (dd, 1H), 6.65 (d, 1H), 6.75 (dd, 1H), 7.14–7.28 (m, 5H), 8.44 (d, 1H), 8.70 (brs, 1H). ESI-MS 513.4 (MH$^+$)

Sweetness, 30000 times the sweetness of sugar

Example 13

Synthesis of N-[N-[3-(3-hydroxy-4-methoxyphenyl)-3-methylbutyl]-L-α-aspartyl]-L-phenylalanine 1-ethyl ester (Table 1, compound number 21)

N-[N-[3-(3-hydroxy-4-methoxyphenyl)-3-methylbutyl]-L-α-aspartyl]-L-phenylalanine 1-ethyl ester was obtained as a solid substance, with a total yield of 56.1%, in the same way as in Example 1, except using N-t-butoxycarbonyl-β-O-benzyl-α-L-aspartyl-L-phenylalanine ethyl ester in place of N-t-butoxycarbonyl-β-O-benzyl-α-L-aspartyl-L-phenylalanine methyl ester.

$^1$HMMR (DMSO-$d_6$) δ: 1.09 1.13 (m, 9H), 1.58–1.67 (m, 2H), 2.08–2.37 (m, 4H), 2.86–2.93 (dd, 1H), 2.99–3.06 (dd, 1H), 3.32–3.37 (m, 1H), 3.71 (s, 3H), 4.00–4.07 (m, 2H), 4.44–4.51 (m, 1H), 6.62–6.65 (d, 1H), 6.74–6.81 (m, 2H), 7.15–7.27 (m, 5H), 8.46 (d, 1H), 8.78 (brs, 1H) ESI-MS 501.3 (MH$^+$)

Sweetness, 15000 times the sweetness of sugar

Example 14

Synthesis of N-[N-[(RS)-3-(3-methoxy-4-hydroxyphenyl) butyl]-L-α-aspartyl]-L-phenylalanine 1-methyl ester (Table 1, compound number 3)

419 mg (1.09 mmol) of β-O-benzyl-α-L-aspartyl-L-phenylalanine methyl ester, obtained in the same way as in Example 1, were dissolved in 10 ml of THF and the resulting solution was maintained at 0° C. To this solution were added 308 mg (1.09 mmol) of 3-β-methoxy-4-benyloxyphenyl)-2-butenal, 0.062 ml (1.09 mmol) of acetic acid and 345 mg (1.63 mmol) of NaB (OAc)$_3$H and the resulting mixture was stirred at 0° C. for one hour and further stirred overnight at room temperature. To the reaction solution were added 30 ml of a saturated aqueous solution of sodium hydrogen carbonate and extraction was carried out twice with 30 ml of ethyl acetate. An organic layer was washed with saturated saline water and dried over anhydrous magnesium sulfate. After filtering magnesium sulfate off, the liquid filtrate was concentrated under reduced pressure. The residue was purified with preparative thin layer chromatography (PTLC) to obtain 534 mg (0.82 mmol) of N-[N-[3-(3-methoxy-4-benzyloxyphenyl)2-butenyl]-β-O-benzyl-L-β-aspartyl]-L-phenylalanine 1-methyl ester as a viscous oily substance.

534 mg (0.82 mmol) of the above N-[N-[3-(3-methoxy-4-benzyloxyphenyl-2-butenyl)-β-O-benzyl-L-αaspartyl]-L-phenylalanine 1-methyl ester were dissolved in a mixed solvent of 20 ml of methanol and 1 ml of water. To the resulting mixture were added 200 mg of 10% palladium carbon (containing 50% of water). The resulting mixture was reduced at room temperature for three hours in a hydrogen atmosphere. The catalyst was filtered off and the resulting filtrate was concentrated under reduced pressure. The residue was purified with PTLC to remove an odor adsorbed to obtain 269 mg (0.57 mmol) of N-[N-[(RS)-3-(3-methoxy-4-hydroxyphenyl) butyl]-L-α-aspartyl]-L-phenylalanine 1-methyl ester as a solid substance.

$^1$HMMR (DMSO-$d_6$) δ: 1.10 (2d, 3H), 1.50–1.60 (m, 2H), 2.10–2.40 (m, 4H), 2.55–2.65 (m, 1H), 2.81–2.95 (m, 1H), 3.03–3.09 (dd, 1H), 3.34–3.40 (m, 1H), 3.60 (s, 1.5H), 3.61 (s, 1.5H), 3.74 (s, 1.5H), 3.75 (s, 1.5H), 4.50–4.60 (m, 1H), 6.55 (d, 1H), 6.67 (d, 1H), 6.72 (s, 1H), 7.15–7.30 (m, 5H), 8.50 (brd, 1H), 8.70 (brs, 1H). ESI-MS 473.3 (MH$^+$)

Sweetness, 30000 times the sweetness of sugar

Example 15

Synthesis of N-[N-[(RS)-3-(4-methoxyphenyl) butyl]-L-α-aspartyl]-L-phenylalanine 1-methyl ester (Table 1, compound number 1)

N-[N-[(RS)-3-(4-methoxyphenyl) butyl]-L-aspartyl]-L-phenylalanine 1-methyl ester was obtained as a solid substance with a total yield of 37.3% in the same way as in Example 14 except using 3-(4-methoxyphenyl)-2-butenal in place of 3-(3-methoxy-4-benzyloxyphenyl)-2-butenal.

$^1$HMMR (DMSO-$d_6$) δ: 1.09 (d, 1.5H), 1.11 (d, 1.5H), 1.54 (m, 2H), 2.17–2.23 (m, 3H), 2.28–2.38 (m, 1H), 2.64 (m, 1H), 2.85–2.95 (m, 1H), 3.02–3.10 (dd, 1H), 3.60 (s, 1.5H). 3.61 (s, 1.5H), 3.70 (s, 1H), 4.54 (m, 1H), 6.83 (d, 2H), 7.07 (d, 2H), 7.18–7.28 (m, 5H). ESI-MS 457.3 (MH$^+$)

Sweetness, 16000 times the sweetness of sugar

Example 16

Synthesis of N-[N-[(RS)-3-(3-hydroxyphenyl) butyl]-L-α-aspartyl]-L-phenylalanine 1 methyl ester (Table 1, compound number 2)

N-[N-[(RS)-3-(3-hydroxyphenyl) butyl]-L-α-aspartyl]-L-phenylalanine 1-methyl ester was obtained as a solid substance with a total yield of 31.1% in the same way as in Example 14 except using 3-(3-benzyloxyphenyl)-2-butenal in place of 3-(3-methoxy-4-benzyloxyphenyl)-2-butenal.

$^1$HMMR (DMSO-$d_6$) δ: 1.09 (m, 3H), 1.55 (m, 2H), 2.10–2.24 (m, 3H), 2.26–2.34 (dd, 1H), 2.58 (m, 1H), 2.85–2.98 (m, 1H), 3.01–3.10 (dd, 1H), 3.60 (s, 1.5H), 3.61 (s, 1.5H), 4.53 (m, 1H), 6.55–6.62 (m, 3H), 7.05 (t, 1H), 7.16–7.30 (m, 5H), 8.47 (m, 1H ), 8.75 (brs, 1H). ESI-MS 443.2 (MH$^+$)

Sweetness, 12000 times the sweetness of sugar

Example 17

Synthesis of N-[N-[(RS)-3-(3-hydroxy-4-methoxyphenyl) butyl]-L-α-aspartyl]-L-phenylalanine 1-methyl ester (Table 1, compound number 4)

N-[N-[(RS)-3-(3-hydroxy-4-methoxyphenyl) butyl]-L-α-aspartyl]-L-phenylalanine 1-methyl ester was obtained as a solid substance with a total yield of 38.8% in the same way as in Example 14 except using 3-(3-benzyloxy-4-methoxyphenyl)-2-butenal in place of 3-(3-methoxy-4-benzyloxyphenyl)-2-butenal.

$^1$HMMR (DMSO-$d_6$) δ: 1.08 (m, 3H), 1.53 (m, 2H), 2.13–2.21 (m, 3H), 2.28 (dd, 1H), 2.56 (m, 1H), 2.86–3.00 (m, 1H), 3.02–3.12 (dd, 1H), 3.29–3.40 (m, 1H), 3.60 (s, 1.5H), 3.61 (s, 1.5H), 3.71 (s, 3H), 4.53 (m, 1H), 6.53 (d, 1H), 6.60 (d, 1H), 6.79 (d, 1H), 7.15–7.26 (m, 5H), 8.46 (m, 1H), 8.75 (brs, 1H). ESI-MS 473.3 (MH$^+$)

Sweetness, 50000 times the sweetness of sugar

Example 18

Synthesis of N-[N-[3-(RS)-3-hydroxy-4-methoxyphenyl) butyl]-L-α-aspartyl]-3-cyclohexyl-L-alanine 1-methyl ester (Table 1, compound number 6)

N-[N-[(RS)-3-(3-hydroxy-4-methoxyphenyl) butyl]-L-α-aspartyl]-3-cyclohexyl-L-alanine 1-methyl ester was obtained as a solid substance with a total yield of 41.7% in the same way as in Example 14 except using N-t-butoxycarbonyl-β-O-benzyl-α-L-aspartyl-3-cyclohexyl-Lalanine methyl ester in place of N-t-butoxycarbonyl-β-O-benzyl-α-L-aspartyl-L-phenylalanine methyl ester and also except using 3-(3-benzyloxy-4-methoxyphenyl)-2-butenal in place of 3-(3-methoxy-4-benzyloxyphenyl)-2-butenal.

$^1$HMMR (DMSO-$d_6$) δ: 0.75–1.34 (m, 5H), 1.11 (d, 3H), 1.50–1.70 (m, 1H), 2.18–2.28 (m, 2H), 2.35–2.45 (m, 2H), 2.58–2.65 (m, 1H), 3.27–3.36 (m, 1H), 3.60 (m, 3H), 3.71 (s, 3H), 4.35 (m, 1H), 6.53–6.60 (m, 1H), 6.61 (d, 1H), 6.79 (d, 1H), 8.44 (m, 1H), 8.80 (brs, 1H). ESI-MS 479.4 (MH$^+$)

Sweetness, 40000 times the sweetness of sugar

Example 19

Synthesis of N-[N-[(RS)-3-(3-methoxy-4-hydroxyphenyl) butyl]-L-α-aspartyl]-L-tyrosine 1-methyl ester (Table 1, compound number 5)

N-[N-[(RS)-3-(3-methoxy-4-hydroxyphenyl)-butyl]-L-α-aspartyl]-L-tyrosine 1-methyl ester was obtained as a solid substance with a total yield of 37.5% in the same way as in Example 14 except using N-t-butoxycarbonyl-β-O-benzyl-α-L aspartyl-L-tyrosine methyl ester in place of N-t-butoxycarbonyl-β-O-benzyl-α-L-aspartyl-L-phenylalanine methyl ester.

$^1$HMMR (DMSO-$d_6$) δ: 1.10 (d, 3H), 1.55 (m, 2H), 2.16–2.41 (m, 4H), 2.58 (m, 1H), 2.70–2.82 (m, 1H), 2.85–2.95 (dd, 1H), 3.58 (s, 3H), 3.78 (s, 3H), 4.43 (m, 1H), 6.53–6.75 (m, 5H), 6.96 (d, 2H), 8.49 (brd, 1H), 8.75 (brs, 1H), 9.80 (brs, 1H) ESI-MS 489.3 (MH$^+$)

Sweetness, 25000 times the sweetness of sugar

Example 20

Synthesis of N-[N-[(RS)-3-(3-methyl-4-hydroxyphenyl) butyl]-L-α-aspartyl]-L-phenylalanine 1-methyl ester (Table 1, compound number 11)

N-[N-[(RS)-3-(3-methyl-4-hydroxy phenyl) butyl]-L-α-aspartyl]-L-phenylalanine 1-methyl ester was obtained as a solid substance with a total yield of 19.7% in the same way as in Example 14 except using 3-(3-methyl-4-benzyloxyphenyl)-2-butenal in place of 3-(3-methoxy-4-benzyloxyphenyl)-2-butenal.

$^1$HMMR (DMSO-$d_6$) δ: 1.06–1.09 (m, 3H), 1.49–1.54 (m, 2H), 2.08 (m, 3H), 2.11–2.20 (m, 3H), 2.17–2.33 (m, 1H), 2.85–2.95 (m, 2H), 3.05–3.09 (m, 1H), 3.33–3.37 (m, 1H), 3.61 (s, 3H), 4.50–4.55 (m, 1H), 6.65 (m, 1H), 6.76 (m, 1H), 6.84 (s, 1H), 7.16–7.28 (m, 5H), 8.47–8.50 (m, 1H), 9.02 (brs, 1H) ESI-MS 457.2 (MH$^+$).

Sweetness, 50000 times the sweetness of sugar

Example 21

Synthesis of N-[N-[3-(3-hydroxy-4-methoxyphenyl)-(RS)-2-methylpropyl)-L-α-aspartyl)-L-phenylalanine 1-methyl ester (Table 1, compound number 12)

N-[N-[3-(3-hydroxy-4-methoxyphenyl)-(RS)-2-methylpropyl]-L-α-aspartyl]-L-phenylalanine 1-methyl ester was obtained as a solid substance with a total yield of 45.6% in the same way as in Example 14 except using 3-(3-benzyloxy-4-methoxyphenyl)-2-methyl-2-propenal in place of 3-(3-methoxy-4-benzyloxyphenyl)-2-butenal.

$^1$HMMR (DMSO-$d_6$) δ: 0.68–0.85 (m, 3H), 1.65–1.82 (m, 1H), 2.08–2.37 (m, 2H), 2.27–2.30 (d, 4H), 2.94–3.10 (m, 2H), 3.43–3.45 (m, 1H), 3.62 (s, 3H), 3.72 (s, 3H), 4.48–4.59 (m, 1H), 6.49–6.59 (m, 2H), 6.77–6.80 (m, 1H), 7.20–7.29 (m, 5H), 8.57–8.58 (m, 1H), 8.92 (brs, 1H). ESI-MS 473.4 (MH$^+$)

Sweetness, 5000 times the sweetness of sugar

Example 22

Synthesis of N-[N-[3-(3-hydroxy-4-methylphenyl)-3-methylbutyl]-L-α-aspartyl]-L-phenylalanine 1-methyl ester (Table 1, compound number 19)

274 mg (0.97 mmol) of 3-[(3-benzyloxy-4-methyl) phenyl]-3-methylbutyl aldehyde, 353 mg (1.2 mmol) of aspartame and 100 mg of 10% palladium carbon (containing 50% of water) were added to 7 ml of methanol and stirred at room temperature for four hours in a hydrogen atmosphere. The catalyst was filtered off and the resulting filtrate was concentrated under reduced pressure. The residue was purified by preparative thin layer chromatography (PTLC) to produce 299 mg (0.64 mmol, 65.5) of N-[N-[3-(3-hydroxy-4-methylphenyl)-3-mehylbutyl]-L-α-aspartyl]-L-phenylalanine 1-methyl ester as a solid substance.

$^1$HMMR (DMSO-$d_6$) δ: 1.14 (s, 6H), 1.58–1.70 (m, 2H), 2.05 (s, 3H), 2.07–242 (m, 4 H), 2.89 (dd, 1H), 3.03 (dd, 1H), 3.30–3.40 (m, 1H), 3.59 (s, 3H), 4.46–4.54 (m, 1H), 6.60 (d, 1H), 6.73 (s, 1H), 6.94 (d, 1H), 7.15–7.30 (m, 5H), 8.46 (brs, 1H) 9.08 (brs, 1H). ESI-MS 471.3 (MH$^+$)

Sweetness, 60000 times the sweetness of sugar

Example 23

Synthesis of N-[N-[3-(3,4-dihydroxyphenyl)-3-mehylbutyl]-L-α-aspartyl]-L-phenylalanine 1-methyl ester (Table 1, compound number 23)

N-[N-[3-(3,4-dihydroxyphenyl)-3-methylbutyl]-L-α-aspartyl]-L-phenylalanine 1-methyl ester was obtained as a solid substance with a total yield of 76.5% in the same way as in Example 1 except using 3-(3,4-dibenzyloxyphenyl)-3methylbutyl aldehide in place of 3-(3-benzyloxy-4-methoxyphenyl)-3-methlbutyl aldehide.

$^1$HMMR (DMSO-$d_6$) δ: 1.14 (s, 6H), 1.76–1.93 (m, 2H), 2.40–2.50 (m, 2H), 2.73–2.80 (m, 2H), 2.91 (dd, 1H), 3.06 (dd, 1H), 3.59 (s, 3H), 3.95–4.05 (m, 1H) 4.45–4.55 (m, 1H), 6.52 (d, 1H), 6.64–6.70 (m, 2H), 6.94 (d, 1H), 7.15–7.30 (m, 5H), 8.73 (brs, 1H), 8.80 (brs, 1H), 9.09 (brs, 1H). ESI-MS 473.3 (MW)

Sweetness, 50000 times the sweetness of sugar

Table 1 shows the structures of several synthesized N-alkyl aspartyl dipeptide ester compounds, shown by the general formula (6) and summarizes the results of the sensory evaluation tests.

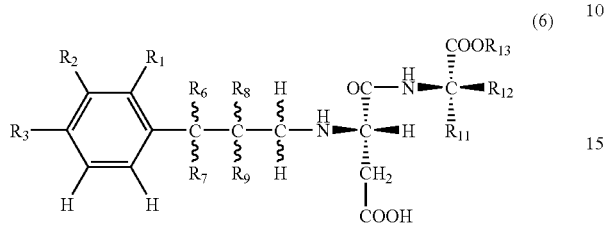

(6)

As is shown by the results in Table 1, the novel compounds of the present invention are particularly excellent in sweetness (sweetening potency).

Structure of N-alkylasparatyl Dipeptide Ester Compound and Sweetness Potency

TABLE 1

| Compound No. | $R_1$ | $R_2$ | $R_3$ | $R_6$ | $R_7$ | $R_8$ | $R_{11}$ | $R_{12}$ | $R_{13}$ | sweetness potency*[1] |
|---|---|---|---|---|---|---|---|---|---|---|
| 1 | H | H | $OCH_3$ | $CH_3$ | H | H | $CH_2C_6H_5$ | H | $CH_3$ | 16000 |
| 2 | H | OH | H | $CH_3$ | H | H | $CH_2C_6H_5$ | H | $CH_3$ | 12000 |
| 3 | H | $OCH_3$ | OH | $CH_3$ | H | H | $CH_2C_6H_5$ | H | $CH_3$ | 30000 |
| 4 | H | OH | $OCH_3$ | $CH_3$ | H | H | $CH_2C_6H_5$ | H | $CH_3$ | 50000 |
| 5 | H | $OCH_3$ | OH | $CH_3$ | H | H | $CH_2C_6H_4$-p-OH | H | $CH_3$ | 25000 |
| 6 | H | OH | $OCH_3$ | $CH_3$ | H | H | $CH_2C_6H11$ | H | $CH_3$ | 40000 |
| 7 | H | H | $OCH_3$ | $CH_3$ | $CH_3$ | H | $CH_2C_6H_5$ | H | $CH_3$ | 25000 |
| 8 | H | H | OH | $CH_3$ | $CH_3$ | H | $CH_2C_6H_5$ | H | $CH_3$ | 25000 |
| 9 | H | $OCH_3$ | OH | $CH_3$ | $CH_3$ | H | $CH_2C_6H_5$ | H | $CH_3$ | 40000 |
| 10 | H | OH | $OCH_3$ | $CH_3$ | $CH_3$ | H | $CH_2C_6H_5$ | H | $CH_3$ | 70000 |
| 11 | H | $CH_3$ | OH | $CH_3$ | H | H | $CH_2C_6H_5$ | H | $CH_3$ | 50000 |
| 12 | H | OH | $OCH_3$ | H | H | $CH_3$ | $CH_2C_6H_5$ | H | $CH_3$ | 5000 |
| 13 | OH | H | H | $CH_3$ | $CH_3$ | H | $CH_2C_6H_5$ | H | $CH_3$ | 8000 |
| 14 | OH | H | $OCH_3$ | $CH_3$ | $CH_3$ | H | $CH_2C_6H_5$ | H | $CH_3$ | 20000 |
| 15 | OH | H | $CH_3$ | $CH_3$ | $CH_3$ | H | $CH_2C_6H_5$ | H | $CH_3$ | 25000 |
| 16 | H | $OCH_2O$ | | $CH_3$ | $CH_3$ | H | $CH_2C_6H_5$ | H | $CH_3$ | 30000 |
| 17 | H | $CH_3$ | $OCH_3$ | $CH_3$ | $CH_3$ | H | $CH_2C_6H_5$ | H | $CH_3$ | 30000 |
| 18 | H | $CH_3$ | OH | $CH_3$ | $CH_3$ | H | $CH_2C_6H_5$ | H | $CH_3$ | 70000 |
| 19 | H | OH | $CH_3$ | $CH_3$ | $CH_3$ | H | $CH_2C_6H_5$ | H | $CH_3$ | 60000 |
| 20 | H | $OCH_3$ | OH | $CH_2CH_2CH_2$ | $CH_2$ | H | $CH_2C_6H_5$ | H | $CH_3$ | 30000 |
| 21 | H | OH | $OCH_3$ | $CH_3$ | $CH_3$ | H | $CH_2C_6H_5$ | H | $CH_2CH_3$ | 15000 |
| 22 | H | OH | $OCH_3$ | $CH_3$ | $CH_3$ | H | $CH_2C_6H_5$ | $CH_3$ | $CH_3$ | 40000 |
| 23 | H | OH | OH | $CH_3$ | $CH_3$ | H | $CH_2C_6H_5$ | H | $CH_3$ | 50000 |

*[1]values compared to sweetening potency of a 4% aqueous solution of sucrose

Effect of Invention

The novel N-alkylaspartyl dipeptide ester compound according to the present invention is low in calories and exhibits a sweetening potency which is particularly superior in comparison with conventional sweetening agents. In the present invention, a novel chemical substance which has superior properties as a sweetening agent can be provided. The novel compound can be used not only for a sweetening agent but also for the affording of sweetness to foods or the like products, such as beverages (drinks) and foods, requiring sweet taste.

Obviously, numerous modifications and variations on the present invention are possible in light of the above teachings. It is therefore to be understood that within the scope of the appended claims, the invention may be practiced otherwise than as specifically described herein.

What is claimed is:

1. An N-alkylaspartyl dipeptide ester compound, and salts thereof, represented by the formula (1):

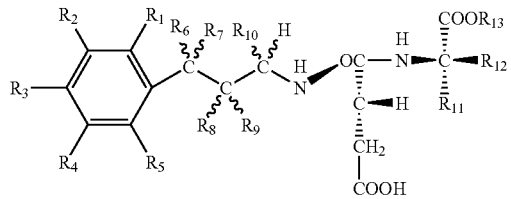

wherein $R_1$, $R_2$, $R_3$, $R_4$ and $R_5$ are independent from each other, selected from the group consisting of a hydrogen atom, a hydroxyl group, an alkoxy group having 1 to 3 carbon atoms, an alkyl group having 1 to 3 carbon atoms and a hydroxy alkyloxy group having two or three carbon atoms, and $R_1$ and $R_2$, or $R_2$ and $R_3$, optionally, form a methylene dioxy group, and $R_4$ and $R_5$, and $R_1$ or $R_3$ which do not form the methylene dioxy group are defined as above;

$R_6$, $R_7$, $R_8$, $R_9$ and $R_{10}$ are independent from each other, a hydrogen atom or an alkyl group with 1 to 3 carbon atoms; and optionally, two of $R_6$, $R_7$, $R_8$, $R_9$ and $R_{10}$ may combine to form an alkylene group with 1 to 5 carbon atoms, and $R_6$, $R_7$, $R_8$, $R_9$ and $R_{10}$ which do not form the alkylene group with 1 to 5 carbon atoms are defined as above;

$R_{11}$ is selected from the group consisting of a hydrogen atom, a benzyl group, a p-hydroxy benzyl group, a cyclohexyl methyl group, a phenyl group, a cyclohexyl group, a phenyl ethyl group and a cyclohexyl ethyl group;

$R_{12}$ is selected from the group consisting of a hydrogen atom and an alkyl group with 1 to 3 carbon atoms; and $R_{13}$ is selected from the group consisting of alkyl groups with 1 to 4 carbon atoms; with the proviso that the following are excluded:

where $R_6$, $R_7$, $R_8$, $R_9$ and $R_{10}$ are hydrogen atoms at the same time, where $R_6$ is a methyl group, $R_1$, $R_2$, $R_3$, $R_4$, $R_5$, $R_7$, $R_8$, $R_9$, $R_{10}$ and $R_{12}$ are a hydrogen atom at the same time and $R_{11}$ is a benzyl group or a p-hydroxy benzyl group, at the same time; and where $R_2$ or $R_4$ is a methoxy group, $R_3$ is a hydroxyl group, $R_{10}$ is a methyl group, $R_1$, $R_4$ or $R_2$, $R_5$, $R_6$, $R_7$, $R_8$ and $R_9$ are hydrogen atoms at the same time, and $R_{11}$ is a benzyl group or a p-hydroxy benzyl group.

2. The compound as defined in claim 1, wherein $R_3$ is a methoxy group, $R_1$, $R_2$, $R_3$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a benzyl group.

3. The compound as defined in claim 1, wherein $R_2$ is a hydroxyl group, $R_1$, $R_3$, $R_4$, $R_5$, $R_7$, $R_8$, $R_9$, $R_{10}$ and $R_{12}$ are hydrogen atoms, $R_6$ and $R_{13}$ are methyl groups, and $R_{11}$ is a benzyl group.

4. The compound as defined in claim 1, wherein $R_2$ is a methoxy group, $R_3$ is a hydroxyl group, $R_1$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a benzyl group.

5. The compound as defined in claim 1, wherein $R_2$ is a hydroxyl group, $R_3$ is a methoxy group, $R_1$, $R_4$, $R_5$, $R_7$, $R_8$, $R_9$, $R_{10}$ and $R_{12}$ are hydrogen atoms, $R_6$ and $R_{13}$ are methyl groups and $R_{11}$ is a benzyl group.

6. The compound as defined in claim 1, wherein $R_2$ is a methoxyl group, $R_3$ is a hydroxy group, $R_1$, $R_4$, $R_5$, $R_7$, $R_8$, $R_9$, $R_{10}$ and $R_{13}$ are hydrogen atoms, $R_6$ and $R_{13}$ are methyl groups and $R_{11}$ is a p-hydroxy benzyl group.

7. The compound as defined in claim 1, wherein $R_2$ is a hydroxyl group, $R_3$ is a methoxy group, $R_1$, $R_4$, $R_5$, $R_7$, $R_8$, $R_9$, $R_{10}$ and $R_{13}$ are hydrogen atoms, $R_6$ and $R_{13}$ are methyl groups and $R_{11}$ is a cyclohexyl methyl group.

8. The compound as defined in claim 1, wherein $R_3$ is a methoxy group, $R_1$, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

9. The compound as defined in claim 1, wherein $R_3$ is a hydroxyl group, $R_1$, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

10. The compound as defined in claim 1, wherein $R_2$ is a methoxy group, $R_3$ is a hydroxyl group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

11. The compound as defined in claim 1, wherein $R_2$ is a hydroxyl group, $R_3$ is a methoxy group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

12. The compound as defined in claim 1, wherein $R_2$ is a methyl group, $R_3$ is a hydroxyl group, $R_1$, $R_4$, $R_5$, $R_7$, $R_8$, $R_9$, $R_{10}$ and $R_{12}$ are hydrogen atoms, $R_6$ and $R_{13}$ are methyl groups, and $R_{11}$ is a benzyl group.

13. The compound as defined in claim 1, wherein $R_2$ is a hydroxyl group, $R_3$ is a methoxy group, $R_1$, $R_4$, $R_5$, $R_6$, $R_7$, $R_9$, $R_{10}$ and $R_{12}$ are hydrogen atoms $R_8$ and $R_{13}$ are methyl groups, and $R_{11}$ is a benzyl group.

14. The compound as defined in claim 1, wherein $R_1$ is a hydroxyl group, $R_2$, $R_3$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

15. The compound as defined in claim 1, wherein $R_1$ is a hydroxyl group, $R_3$ is a methoxy group, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

16. The compound as defined in claim 1, wherein $R_1$ is a hydroxyl group, $R_3$ is a methyl group, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

17. The compound as defined in claim 1, wherein $R_2$ and $R_3$ combine to form a methylene dioxy group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

18. The compound as defined in claim 1, wherein $R_2$ is a methyl group, $R_3$ is a methoxy group, $R_1$, $R_4$, $R_5$, $R_8$, $R_9$, $R_{10}$ and $R_{12}$ are hydrogen atoms, $R_6$, $R_7$, and $R_{13}$ are methyl groups, and $R_{11}$ is a benzyl group.

19. The compound as defined in claim 1, wherein $R_2$ is a methyl group, $R_3$ is a hydroxyl group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

20. The compound as defined in claim 1, wherein $R_2$ is a hydroxyl group, $R_3$ is a methyl group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

21. The compound as defined in claim 1, wherein $R_2$ is a methoxy group, $R_3$ is a hydroxyl group, $R_1$, $R_4$, $R_5$, $R_8$, $R_9$, $R_{10}$ and $R_{12}$ are hydrogen atoms, $R_6$ and $R_7$ combine to form a tetramethylene group, $R_{11}$ is a benzyl group, and $R_{13}$ is a methyl group.

22. The compound as defined in claim 1, wherein $R_2$ is a hydroxyl group, $R_3$ is a methoxy group, $R_1$, $R_4$, $R_5$, $R_8$, $R_9$, $R_{10}$ and $R_{12}$ are hydrogen atoms, $R_6$ and $R_7$ are methyl groups, $R_{11}$ is a benzyl group, and $R_{13}$ is an ethyl group.

23. The compound as defined in claim 1, wherein $R_2$ is a hydroxyl group, $R_3$ is a methoxy group, $R_1$, $R_4$, $R_5$, $R_8$, $R_9$ and $R_{10}$ are hydrogen atoms, $R_6$, $R_7$, $R_{12}$ and $R_{13}$ are methyl groups, and $R_{11}$ is a benzyl group.

24. The compound as defined in claim 1, wherein $R_2$ and $R_3$ is a hydroxyl group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

25. The compound as defined in claim 1, wherein when $R_6$ and $R_7$ differ, the carbon atom to which $R_6$ is linked in said formula is in the (R), (S) or (RS) configuration.

26. The compound as defined in claim 1, wherein when $R_8$ and $R_9$ differ, the carbon atom to which $R_8$ is linked is in the (R), (S) or (RS) configuration.

27. The compound as defined in claim 13, wherein when $R_8$ and $R_9$ differ the carbon atom to which $R_8$ is linked is in the (R), (S) or (RS) configuration.

28. The compound as defined in claim 1, wherein when $R_{10}$ is a substituent other than a hydrogen atom, the configuration of the carbon atom to which $R_{10}$ is linked in said formula (1) is in the (R), (S) or (RS) configuration.

29. A composition comprising at least one compound of claim 1 and a carrier or bulking agent.

30. A method of imparting sweetness into a substance comprising adding at least one compound of claim 1 to said substance, wherein said substance is selected from the group consisting of a food item, a beverage, a soft-drink, a fruit juice, a tea, water, a confectionery, chewing gum, a hygiene product, a toiletry, a cosmetic, a pharmaceutical product and a veterinary product.

31. A method of producing the compound as defined in claim 1, wherein $R_{10}$ is a hydrogen atom comprising:

reacting under reductive alkylation conditions an aldehyde having the formula (2):

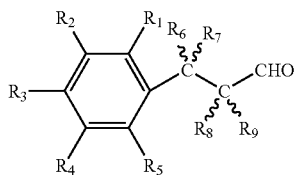
(2)

wherein $R_1, R_2, R_3, R_4, R_5, R_6, R_7, R_8$ and $R_9$ have the same meanings as $R_1, R_2, R_3, R_4, R_5, R_6, R_7, R_8$ and $R_9$, respectively in the above formula (1), with en aspartame compound having the formula (3):

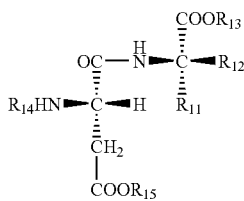
(3)

wherein $R_{11}, R_{12}$ and $R_{13}$ in formula (3) have the same meanings as $R_{11}, R_{12}$ and $R_{13}$ in formula (1), $R_{14}$ is a hydrogen atom or a substituent which can be converted into a hydrogen atom and $R_{15}$ is a hydrogen atom, benzyl group or a substituent which may be used to protect a carboxyl group.

32. The method as defined in claim 1, wherein $R_{15}$ is a t-butyl group.

33. A method of producing the compound as defined in claim 1, wherein $R_7$, $R_9$ and $R_{10}$ are a hydrogen atom comprising:

reacting under reductive alkylation conditions an aldehyde having the formula (4):

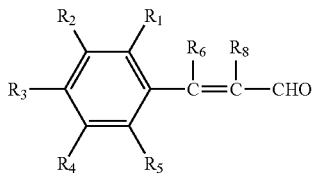
(4)

with an aspartame compound having the formula (3):

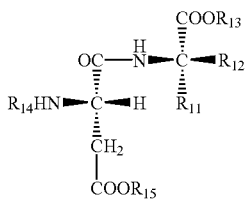
(3)

wherein $R_{11}, R_{12}$ and $R_{13}$ in formula (3) have the same meanings as $R_{11}, R_{12}$ and $R_{13}$ in formula (1), $R_{14}$ is a hydrogen atom or a substituent which can be converted into a hydrogen atom and $R_{15}$ is a hydrogen atom, benzyl group or a substituent which may be used to protect a carboxyl group.

34. A method of producing the compound as defined in claim 1, comprising:

reacting under reductive alkylation conditions an aldehyde having the formula (5):

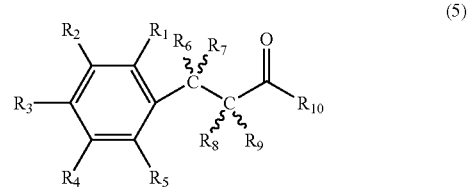
(5)

wherein $R_1, R_2, R_3, R_4, R_5, R_6, R_7, R_8, R_9$ and $R_{10}$ have the same meanings as $R_1, R_2, R_3, R_4, R_5, R_6, R_7, R_8, R_9$ and $R_{10}$, respectively in formula (1);

with an aspartame compound having the formula (3):

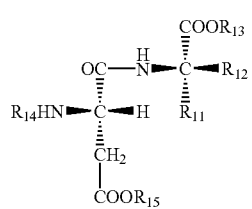
(3)

wherein $R_{11}, R_{12}$ and $R_{13}$ in formula (3) have the same meanings as $R_{11}, R_{12}$ and $R_{13}$ in formula (1), $R_{14}$ is a hydrogen atom or a substituent which can be converted into a hydrogen atom and $R_{15}$ is a hydrogen atom, benzyl group or a substituent which may be used to protect a carboxyl group.

35. The composition according to claim 29, wherein said carrier or bulking agent is one or more compounds selected from the group consisting of polydextrose, starch, maltodextrines, cellulose, methylcellulose, carboxymethylcellulose and other cellulose compounds, sodium alginate, pectins, gums, lactose, maltose, glucose, sucrose, leucine, glycerole, mannitol, sorbitol, xylitol, and erythritol.

36. The method of claim 34, wherein $R_3$ is a methoxy group, $R_1, R_2, R_3, R_4, R_5, R_7, R_8, R_9, R_{10}$ and $R_{12}$ are hydrogen atoms, $R_6$ and $R_{13}$ are methyl groups and $R_{11}$ is a benzyl group.

37. The method of claim 34, wherein $R_2$ is a hydroxyl group, $R_1, R_3, R_4, R_5, R_7, R_8, R_9, R_{10}$ and $R_{12}$ are hydrogen atoms, $R_6$ and $R_{13}$ are methyl groups, and $R_{11}$ is a benzyl group.

38. The method of claim 34, wherein $R_2$ is a methoxy group, $R_3$ is a hydroxyl group, $R_1, R_4, R_5, R_7, R_8, R_9, R_{10}$ and $R_{12}$ are hydrogen atoms, $R_6$ and $R_{13}$ are methyl groups and $R_{11}$ is a benzyl group.

39. The method of claim 34, wherein $R_2$ is a hydroxyl group, $R_3$ is a methoxy group, $R_1, R_4, R_5, R_7, R_8, R_9, R_{10}$ and $R_{12}$ are hydrogen atoms, $R_6$ and $R_{13}$ are methyl groups and $R_{11}$ is a benzyl group.

40. The method of claim 34, wherein $R_2$ is a methoxyl group, $R_3$ is a methoxy group, $R_1, R_4, R_5, R_7, R_8, R_9, R_{10}$ and $R_{12}$ are hydrogen atoms, $R_6$ and $R_{13}$ are methyl groups and $R_{11}$ is a p-hydroxy benzyl group.

41. The method of claim 34, wherein $R_2$ is a hydroxyl group, $R_3$ is a methoxy group, $R_1, R_4, R_5, R_7, R_8, R_9, R_{10}$ and $R_{12}$ are hydrogen atoms, $R_6$ and $R_{13}$ are methyl groups and $R_{11}$ is a cyclohexyl methyl group.

42. The method of claim 34, wherein $R_3$ is a methoxy groups, $R_1, R_2, R_4, R_5, R_8, R_9, R_{10}$ and $R_{12}$ are hydrogen atoms, $R_6, R_7$ and $R_{13}$ are methyl groups, and $R_{11}$ is a benzyl group.

43. The method of claim 34, wherein $R_3$ is a hydroxyl groups, $R_1$, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

44. The method of claim 34, wherein $R_2$ is a methoxy group, $R_3$ is a hydroxyl group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

45. The method of claim 34, wherein $R_2$ is a hydroxyl group, $R_3$ is a hydroxyl group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

46. The method of claim 34, wherein $R_2$ is a methyl group, $R_3$ is a hydroxyl group, $R_1$, $R_4$, $R_5$, $R_7$, $R_8$, $R_9$, $R_{10}$ and $R_{12}$ are hydrogen atoms, $R_6$ and $R_{13}$ are methyl groups, and $R_{11}$ is a benzyl group.

47. The method of claim 34, wherein $R_2$ is a hydroxyl group, $R_3$ is a methoxy group, $R_1$, $R_4$, $R_5$, $R_6$, $R_7$, $R_9$, $R_{10}$ and $R_{12}$ are hydrogen atoms, $R_8$ and $R_{13}$ are methyl groups, and $R_{11}$ is a benzyl group.

48. The method of claim 34, wherein $R_1$ is a hydroxyl group, $R_2$, $R_3$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

49. The method of claim 34, wherein $R_1$ is a hydroxyl group, $R_3$ is a methoxy group, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

50. The method of claim 34, wherein $R_1$ is a hydroxyl group, $R_3$ is a methyl group, $R_2$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

51. The method of claim 34, wherein $R_2$ and $R_3$ combine to form a methylene dioxy group, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

52. The method of claim 34, wherein $R_2$ is a methyl group, $R_3$ is a methoxy group, $R_1$, $R_4$, $R_5$, $R_8$, $R_9$, $R_{10}$ and $R_{12}$ are hydrogen atoms, $R_6$, $R_7$, and $R_{13}$ are methyl groups, and $R_{11}$ is a benzyl group.

53. The method of claim 34, wherein $R_2$ is a methyl group, $R_3$ is a hydroxyl group, $R_1$, $R_4$, $R_5$, $R_8$, $R_9$, $R_{10}$ and $R_{12}$ are hydrogen atoms, $R_6$, $R_7$, and $R_{13}$ are methyl groups, and $R_{11}$ is a benzyl group.

54. The method of claim 34, wherein $R_2$ is a hydroxyl group, $R_3$ is a methoxy group, $R_1$, $R_4$, $R_5$, $R_8$, $R_9$, $R_{10}$ and $R_{12}$ are hydrogen atoms, $R_6$, $R_7$, and $R_{13}$ are methyl groups, and $R_{11}$ is a benzyl group.

55. The method of claim 34, wherein $R_2$ is a methoxy group, $R_3$ is a hydroxy group, $R_1$, $R_4$, $R_5$, $R_8$, $R_9$, $R_{10}$ and $R_{12}$ are hydrogen atoms, $R_6$, $R_7$ combine to form a tetramethylene group, $R_{11}$ is a benzyl group, and $R_{13}$ is a methyl group.

56. The method of claim 34, wherein $R_2$ is a hydroxyl group, $R_3$ is a methoxy group, $R_1$, $R_4$, $R_5$, $R_8$, $R_9$, $R_{10}$ and $R_{12}$ are hydrogen atoms, $R_6$ and $R_7$ are methyl groups, $R_{11}$ is a benzyl group, and $R_{13}$ is an ethyl group.

57. The method of claim 34, wherein $R_2$ is a hydroxyl group, $R_3$ is a methoxy group, $R_1$, $R_4$, $R_5$, $R_8$, $R_9$ and $R_{10}$ are hydrogen atoms, $R_6$, $R_7$, $R_{12}$ and $R_{13}$ are methyl groups, and $R_{11}$ is a benzyl group.

58. The method of claim 34, wherein $R_2$ and $R_3$ are hydroxyl groups, $R_1$, $R_4$, $R_5$, $R_8$, $R_9$, $R_{10}$ and $R_{12}$ are hydrogen atoms, $R_6$, $R_7$ and $R_{13}$ are methyl groups, and $R_{11}$ is a benzyl group.

59. The method of claim 34, wherein when $R_6$ and $R_7$ differ, the carbon atom to which $R_6$ is linked in said formula is in the (R), (S) or (RS) configuration.

60. The method of claim 34, wherein when $R_8$ and $R_9$ differ, the carbon atom to which $R_8$ is linked is in the (R), (S) or (RS) configuration.

61. The method of claim 47, wherein when $R_8$ and $R_9$ differ, the carbon atom to which $R_8$ is linked is in the (R), (S) or (RS) configuration.

62. The method of claim 34, wherein when $R_{10}$ is a substituent other than a hydrogen atom, the configuration of the carbon atom to which $R_{10}$ is linked in said formula (1) is in the (R), (S) or (RS) configuration.

\* \* \* \* \*

UNITED STATES PATENT AND TRADEMARK OFFICE
CERTIFICATE OF CORRECTION

PATENT NO. : 7,238,830 B2
APPLICATION NO. : 09/809197
DATED : July 3, 2007
INVENTOR(S) : Yusuke Amino et al.

It is certified that error appears in the above-identified patent and that said Letters Patent is hereby corrected as shown below:

Column 1, line 8, "This invention relates to a novel N-alkylaspartyl dipeptide"
 should read -- This invention relates to novel N-alkylaspartyl dipeptide --;
 line 18, "the development of a low-calory sweetener"
 should read -- the development of a low-calorie sweetener --;
 line 65, "group on the the propyl group."
 should read -- group on the propyl group. --.

Column 2, line 4, "development of a low-calory"
 should read -- development of a low-calorie --;
 line 8, "problems associated with prior low-calory"
 should read -- problems associated with prior low-calorie --;
 line 11, "and a low-calory sweetening agent"
 should read -- and a low-calorie sweetening agent --.
 lines 24-26, "
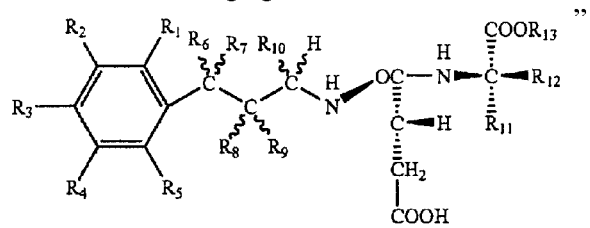
"
 should read --
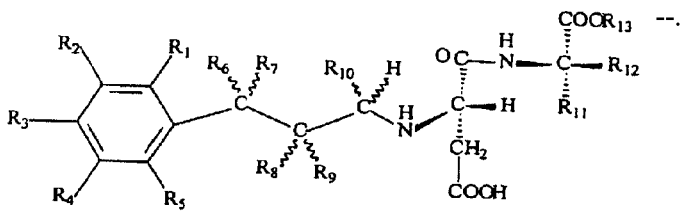
 --.

Column 3, line 12, "of 3-(substituted phenyl) propyl group,"
 should read -- of 3-(substituted phenyl) propyl groups, --.

Column 4, line 12, "one to three carbon atom,"
 should read -- one to three carbon atoms, --;
 line 32, -- "$R_6$ and $R_{13}$ are a methyl"
 should read -- $R_6$ and $R_{13}$ are methyl --;
 line 50, -- "$R_6$, $R_7$ and $R_{13}$ are a methyl"
 should read -- $R_6$, $R_7$ and $R_{13}$ are methyl --.

UNITED STATES PATENT AND TRADEMARK OFFICE
CERTIFICATE OF CORRECTION

PATENT NO.       : 7,238,830 B2
APPLICATION NO.  : 09/809197
DATED            : July 3, 2007
INVENTOR(S)      : Yusuke Amino et al.

It is certified that error appears in the above-identified patent and that said Letters Patent is hereby corrected as shown below:

line 57, "$R_{13}$ are methyl group sand $R_{11}$ is a benzyl group."
  should read -- $R_{13}$ are methyl groups and $R_{11}$ is a benzyl group. --.

Column 7, line 20, "conditions, an aldehyde having formula (5):"
  should read -- conditions, an aldehyde having the formula (5): --.

Column 9, line 17, "incorporated by reference into the present specification"
  should read -- incorporated by reference into the present specification. --.

Column 11, line 28, "2.18-238 (m, 4H),"
  should read -- 2.18-2.38 (m, 4H), --.

Column 13, line 46, "1.09 1.13 (m, 9H),"
  should read -- 1.09-1.13 (m, 9H), --.

Column 14, line 9, "benzyloxyphenyl)2-butenyl]-β-O-benzyl-L-β-aspartyl]-L-"
  should read -- benzyloxyphenyl)2-butenyl]-β-O-benzyl-L-α-aspartyl]-L- --;
      line 12, "4-benzyloxyphenyl-2-butenyl)-β-O-benzyl-L-αaspartyl]-L-"
  should read -- 4-benzyloxyphenyl-2-butenyl)-β-O-benzyl-L-α-aspartyl]-L- --.

Column 15, line 25, "Lalanine methyl ester in place of"
  should read -- L-alanine methyl ester in place of --.

Column 16, line 44, "4-methylphenyl)-3-mehylbutyl]-L-α-aspartyl]-L-"
  should read -- 4-methylphenyl)-3-methylbutyl]-L-α-aspartyl]-L- --;
      line 47, "2.07-242 (m, 4 H),"
  should read -- 2.07-2.42 (m, 4 H), --;
      line 57, "mehylbutyl]-L-α-aspartyl]-L-phenylalanine 1-"
  should read -- methylbutyl]-L-α-aspartyl]-L-phenylalanine 1- --;
      line 63, "3methylbutyl aldehide in place of"
  should read -- 3methylbutyl aldehyde in place of --;
      line 64, "methoxyphenyl)-3-methylbutyl aldehide."
  should read -- methoxyphenyl)-3-methylbutyl aldehyde. --.

UNITED STATES PATENT AND TRADEMARK OFFICE
CERTIFICATE OF CORRECTION

PATENT NO. : 7,238,830 B2
APPLICATION NO. : 09/809197
DATED : July 3, 2007
INVENTOR(S) : Yusuke Amino et al.

Page 3 of 4

It is certified that error appears in the above-identified patent and that said Letters Patent is hereby corrected as shown below:

Column 18, lines 8-13, " 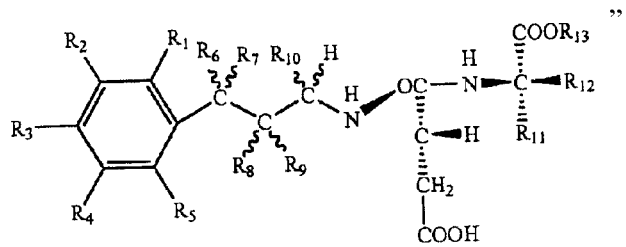 "

should read -- 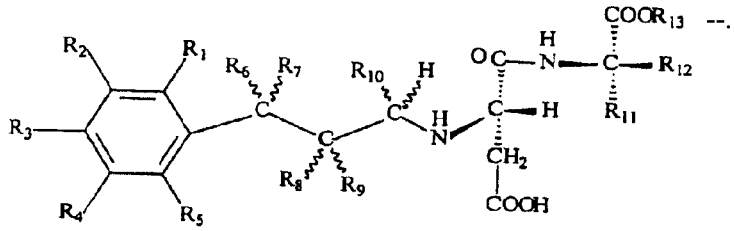 --.

Column 19, line 30, "$R_9$, $R_{10}$ and $R_{13}$ are hydrogen atoms,"
    should read -- $R_9$, $R_{10}$ and $R_{12}$ are hydrogen atoms, --;
        line 34, "$R_9$, $R_{10}$ and $R_{13}$ are hydrogen atoms,"
    should read -- $R_9$, $R_{10}$ and $R_{12}$ are hydrogen atoms, --;

Column 20, line 37, "$R_3$ is a hydroxyl group,"
    should read -- $R_3$ are hydroxyl groups, --.

Column 21, line 13, "$R_9$, respectively in the above formula (1), with en"
    should read -- $R_9$, respectively in the above formula (1), with an --;
        line 28, "into a hydrogen atom and $R_{15}$ is a hydrogen atom,"
    should read -- into a hydrogen atom under hydrogenation conditions and $R_{15}$ is a
            hydrogen atom, --;
        line 63, "into a hydrogen atom and $R_{15}$ is a hydrogen atom,"
    should read -- into a hydrogen atom under hydrogenation conditions and $R_{15}$ is a
            hydrogen atom, --;

Column 22, line 31, "into a hydrogen atom and $R_{15}$ is a hydrogen atom,"
    should read -- into a hydrogen atom under hydrogenation conditions and $R_{15}$ is a
            hydrogen atom, --;
        line 57, "$R_3$ is a methoxy group,"
    should read -- $R_3$ is a hydroxy group, --;
        line 65, "groups, $R_1$, $R_2$, $R_4$, $R_5$, $R_8$, $R_9$, $R_{10}$ and $R_{12}$ are hydrogen"
    should read -- group, $R_1$, $R_2$, $R_4$, $R_5$, $R_8$, $R_9$, $R_{10}$ and $R_{12}$ are hydrogen --.

UNITED STATES PATENT AND TRADEMARK OFFICE
CERTIFICATE OF CORRECTION

PATENT NO.       : 7,238,830 B2
APPLICATION NO.  : 09/809197
DATED            : July 3, 2007
INVENTOR(S)      : Yusuke Amino et al.

It is certified that error appears in the above-identified patent and that said Letters Patent is hereby corrected as shown below:

Column 23, line 10, "$R_3$ is a hydroxyl group,"
  should read -- $R_3$ is a methoxy group, --.

Column 24, line 10, "$R_3$ is a hydroxy group,"
  should read -- $R_3$ is a hydroxyl group, --;
    line 11, "$R_6$, $R_7$ combine to form a"
  should read -- $R_6$ and $R_7$ combine to form a --.

Signed and Sealed this

Eleventh Day of March, 2008

JON W. DUDAS
*Director of the United States Patent and Trademark Office*